United States Patent
Wong

(10) Patent No.: US 6,845,537 B2
(45) Date of Patent: Jan. 25, 2005

(54) AUTOMATIC POWER-DRIVEN TOOTHBRUSHES

(76) Inventor: Man-Kwan Wong, Wah Ha Industrial Building, 15F, Blk C 8 Shipyard Lane, Quarry Bay (HK)

(*) Notice: Subject to any disclaimer, the term of this patent is extended or adjusted under 35 U.S.C. 154(b) by 213 days.

(21) Appl. No.: 10/068,338

(22) Filed: Feb. 6, 2002

(65) Prior Publication Data

US 2002/0116775 A1 Aug. 29, 2002

Related U.S. Application Data

(60) Provisional application No. 60/267,171, filed on Feb. 6, 2001.

(51) Int. Cl.⁷ .......................... A46B 13/00; H02K 41/00
(52) U.S. Cl. .......................... 15/22.1; 15/22.2; 15/21.1; 310/12
(58) Field of Search .................... 15/21.1, 22.1–22.2, 15/22.4, 28; 310/81, 12

(56) References Cited

U.S. PATENT DOCUMENTS

| | | | |
|---|---|---|---|
| 5,189,751 A | * | 3/1993 | Giuliani et al. ............... 15/22.1 |
| 6,140,723 A | * | 10/2000 | Matsui et al. .................. 310/81 |
| 2002/0084707 A1 | * | 7/2002 | Tang ............................ 310/81 |
| 2002/0092104 A1 | * | 7/2002 | Ferber et al. ................. 15/22.1 |

* cited by examiner

Primary Examiner—Terrence R. Till
Assistant Examiner—Laura C Cole
(74) Attorney, Agent, or Firm—Bo-In Lin

(57) ABSTRACT

The present invention discloses the present invention discloses a power toothbrush that includes a body portion 105. An elongated level arm 102 extends from one end of the body portion to a toothbrush head 101 disposed at a distal end of the toothbrush. The toothbrush head includes a plurality of brush bristles. The elongated lever arm 102 is mounted on a vibrating pivot 104 driven by rotational DC motor engaging and pushing a set of permanent magnets attached to a two-arm fork rotating along the lever arm 102. In a preferred embodiment, the DC motor drives a three-leg permanent magnets each disposed at a 120-degree phase from each other for driving the two-arm fork for generating a vibration that three-times the frequency of the DC motor's rotational frequency.

4 Claims, 10 Drawing Sheets

AUTOMATIC POWER-DRIVEN TOOTHBRUSHES

This Application claims a priority date of Feb. 6, 2001 benefited from a previously filed Provisional Patent Application No. 60/267,171 filed on Feb. 6, 2001 by a same Applicant of this Formal Patent Application.

BACKGROUND OF THE INVENTION

1. Field of the Invention

This invention relates generally to a dental hygiene device. More particularly, this invention relates to an electromagnetic power-driven toothbrush provided with improved electromagnetic-and-mechanical-coupled driving mechanisms and a novel and improved battery charging device with significantly higher charging efficiency.

2. Description of the Prior Art

Several major limitations are faced by the manufacturers and designers of conventional vibrating or rotating toothbrushes driven by forces generated with input signals of continuously pulsed or alternating electromagnetic signals. A first limitation is the difficulties in generating higher frequency of bristle movements to effectively remove dental plagues by brushing and acoustic cleaning. Conventional power driven toothbrushes typically have difficulties in providing frequency of bristle movement higher than 10,000 cycles per minutes. Technical limitations and cost considerations often prevent the frequency of a conventional automatic toothbrush to exceed a limit higher than 10,000 cycles per minute. In addition to the limitations encountered for providing higher frequencies of movement, a feature of frequency control and adjustment when implemented in conventional toothbrushes would often require more complicate electromagnetic and mechanical designs and become quite costly. Typically, the power-driven toothbrushes are provided only with on-and-off switches. Due to the cost consideration, generally, there is no user control or adjustment of brushing speed. Furthermore, as rechargeable batteries are commonly used in the automatic power-driven toothbrushes, the application of the power-driven toothbrushes is often limited by requiring long period of recharging operation. Such long hours of recharge requirement is caused by the low charging rates due to the ineffective battery charging methods commonly employed in conventional electric toothbrushes now available in the marketplace.

An example of conventional vibrating toothbrushes is disclosed by Giuliani et al. disclose in U.S. Pat. No. 5,189,751, entitled "Vibrating Toothbrush Using A Magnetic Driver" (issued on Mar. 2, 1993). The vibrating toothbrush includes a toothbrush body and a lever arm that includes toothbrush bristles. The lever arm is mounted for pivotal movement at a pivot member. FIGS. 1A to 1D are exemplary drawings from the issued patents of Giuliani, et. al for illustrating typical conventional methods of converting electric energy provided by the rechargeable battery 38 into driving forces for vibrating the lever arm 14 and the toothbrush bristles 15. As shown in FIGS. 1A to 1D, a pair of permanent magnets, e.g., magnets 44 and 46 in FIG. 1B or magnets 111 and 112 in FIG. 1D, is provided at the other end of the lever arm positioned side by side with opposite polarities. Immediately next to the pair of magnets is an electromagnet, e.g., E-core electromagnet 24 or U-shaped electromagnet 116. The electromagnet receives an alternating signals from an oscillating circuit 40 having a frequency of 150 to 400 Hz with the rechargeable battery 38 functions as a power supply for the oscillating circuit 40. As the alternating signals from the oscillator drive the electromagnets to continuously change polarities, a clockwise followed by counter-clockwise vibrations are generated because of the retraction and repulsion forces generated between the permanent magnets and the electromagnets. The driving forces generated by coupling the magnetic fields between the permanent magnets and the electromagnets are however inefficient utilization of the energy provided by the rechargeable battery. The inefficiency of energy utilization is the results of energy losses in the air gap fluxes between the permanent magnets and the electromagnets. Additionally, the maximum frequency is limited to the frequency of the oscillator. Due to the constraints of the output voltage of the rechargeable battery, the maximum frequency of the oscillator is limited. Thus a higher frequency of bristle movement is difficult to achieve because the limitation of the frequency of the oscillating circuit.

Therefore, a need still exists for a new system configuration and design method in the art of automatic power driven toothbrushes to resolve these difficulties and limitations. More particularly, this new system configuration and design approach must be able to reduce the energy loss by more directly coupling the driving mechanisms provided by the battery to the lever arm connected to the toothbrush bristles. Preferably, the driving mechanism may be provided to generate output vibrations or rotations at higher frequencies than an input frequency driven by the energy provided by the battery. In addition to providing power driven toothbrushes with higher speed of bristle movements, a need also exists to more efficiently charge the battery. With improved charging circuit of this invention, the required recharging period can then be shortened and the need to purchase several automatic toothbrushes when shared by several users in a household can be eliminated with more powerful and efficient charging circuit to charge the rechargeable battery.

SUMMARY OF THE PRESENT INVENTION

It is therefore an object of the present invention to provide an automatic power toothbrush capable of vibrating or rotating at higher frequency and can be charged with higher charging capacities such that the aforementioned difficulties encountered in the prior art can be overcome.

Specifically, it is an object of the present invention to provide an improved automatic power toothbrush driven by a direct coupling of the mechanical rotation to the electromagnetic force to generate vibrations of higher frequencies. More direct and efficient utilization of electric power is achieved with the DC motor rotation movement powered by the rechargeable batteries. Higher vibrating frequencies are also made available by employing this improved driving mechanism.

Another object of the present invention is to provide an improved automatic power toothbrush charged by a direct AC-to-AC current transformer charging circuit to provide higher charging capacity. The charging efficiency is further improved and optimized with a frequency converter to convert a regular AC current to a primary current of higher frequency to generate a secondary induced current applicable for efficiently charging the rechargeable batteries. Shorter charging period is achieved with higher charging capacity. The toothbrush can then be more economically employed by multiple users with multiple brush head when the charging period is shortened.

Another object of the present invention is to provide an improved automatic power toothbrush driven by a direct mechanical to electromagnetic driving mechanism. More direct and convenient control of the vibrating speed is now achievable by simply varying the rotational speed of the DC motor. The user is provided with more convenient options to vary the brushing speed by a speed variation control switch with more precise control mechanism because the direct mechanical to electromagnetic coupling in driving the power toothbrush.

Briefly, in a preferred embodiment, the present invention discloses a power toothbrush that includes a body portion 105. An elongated level arm 102 extends from one end of the body portion to a toothbrush head 101 disposed at a distal end of the toothbrush. The toothbrush head includes a plurality of brush bristles. The elongated lever arm 102 is mounted on an vibrating pivot 104 driven by rotational DC motor engaging and pushing a set of permanent magnets attached to a two-arm fork rotating along the lever arm 102. In a preferred embodiment, the DC motor drives a three-leg permanent magnets each disposed at a 120-degree phase from each other for driving the two-arm fork for generating a vibration that three-times the frequency of the DC motor's rotational frequency. A power toothbrush capable of vibrating at a frequency of 15,000 to 20,000 cycles per minute is disclosed in this invention. Furthermore, in another preferred embodiment, this invention also discloses an improved battery-charging configuration. The charging circuit for the battery provides a rectified DC current of 160 mA to the battery by configuring the charging circuit as a secondary transformer circuit with the primary circuit connected to a frequency converter for providing high frequency input AC current as primary current for induced the secondary current. A highly efficient charging configuration is disclosed and the batteries of the toothbrush can be fully charged in about six hours instead of 16 to 24 hours required by a conventional power toothbrush.

These and other objects and advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

Figure 1A:
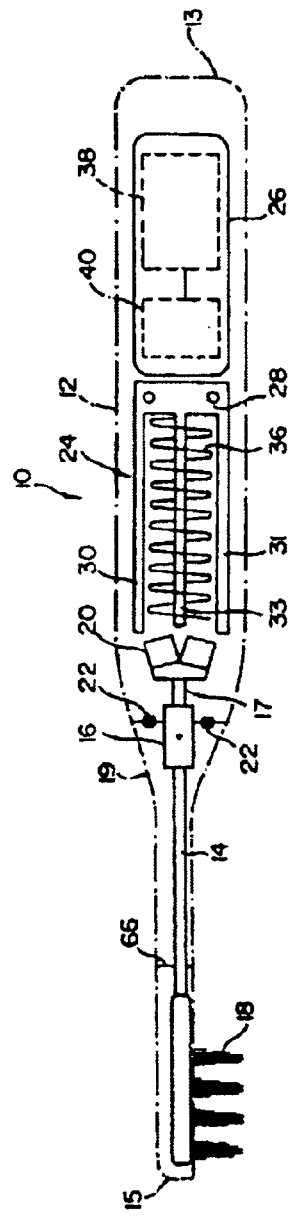
FIGS. 1A to 1D are cross sectional views of a prior art power toothbrush driven by conventional electromagnetic techniques dictated by electric pulses and the induced magnetic fields variations.
Figure 1B:
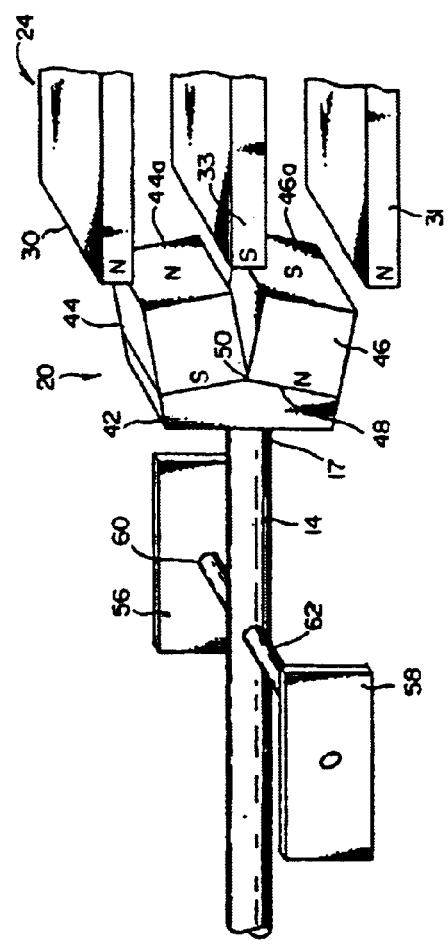
Figure 1C:
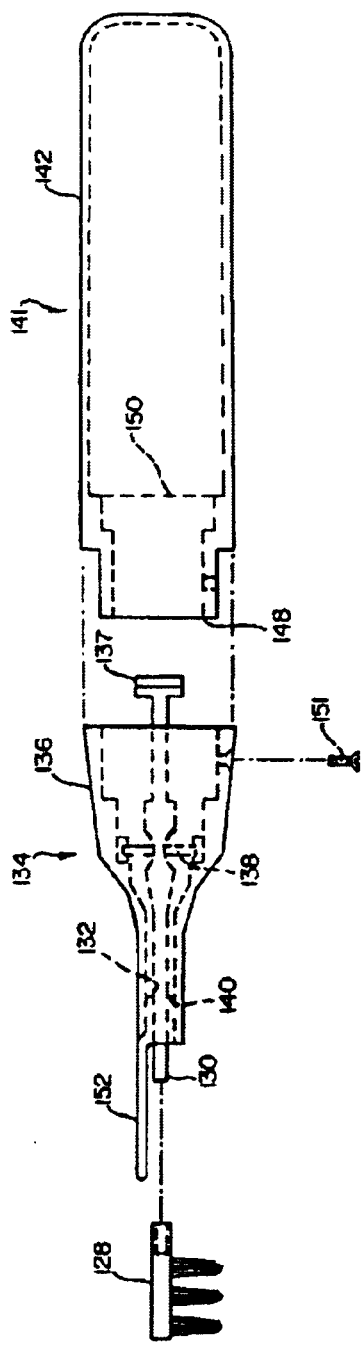
Figure 1D:
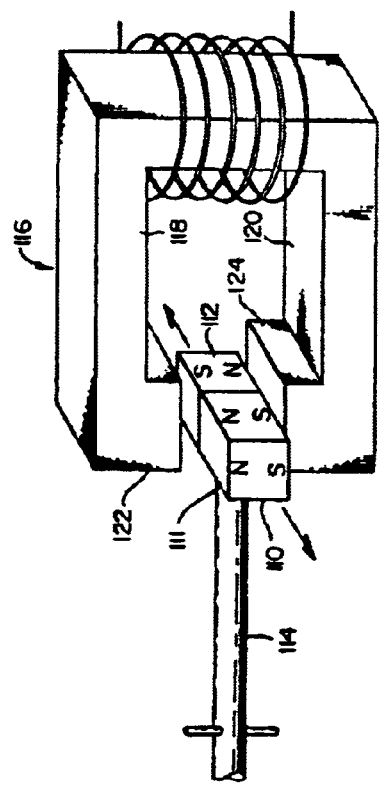
Figures 2A, 2B, 2C, 2D, 2E:
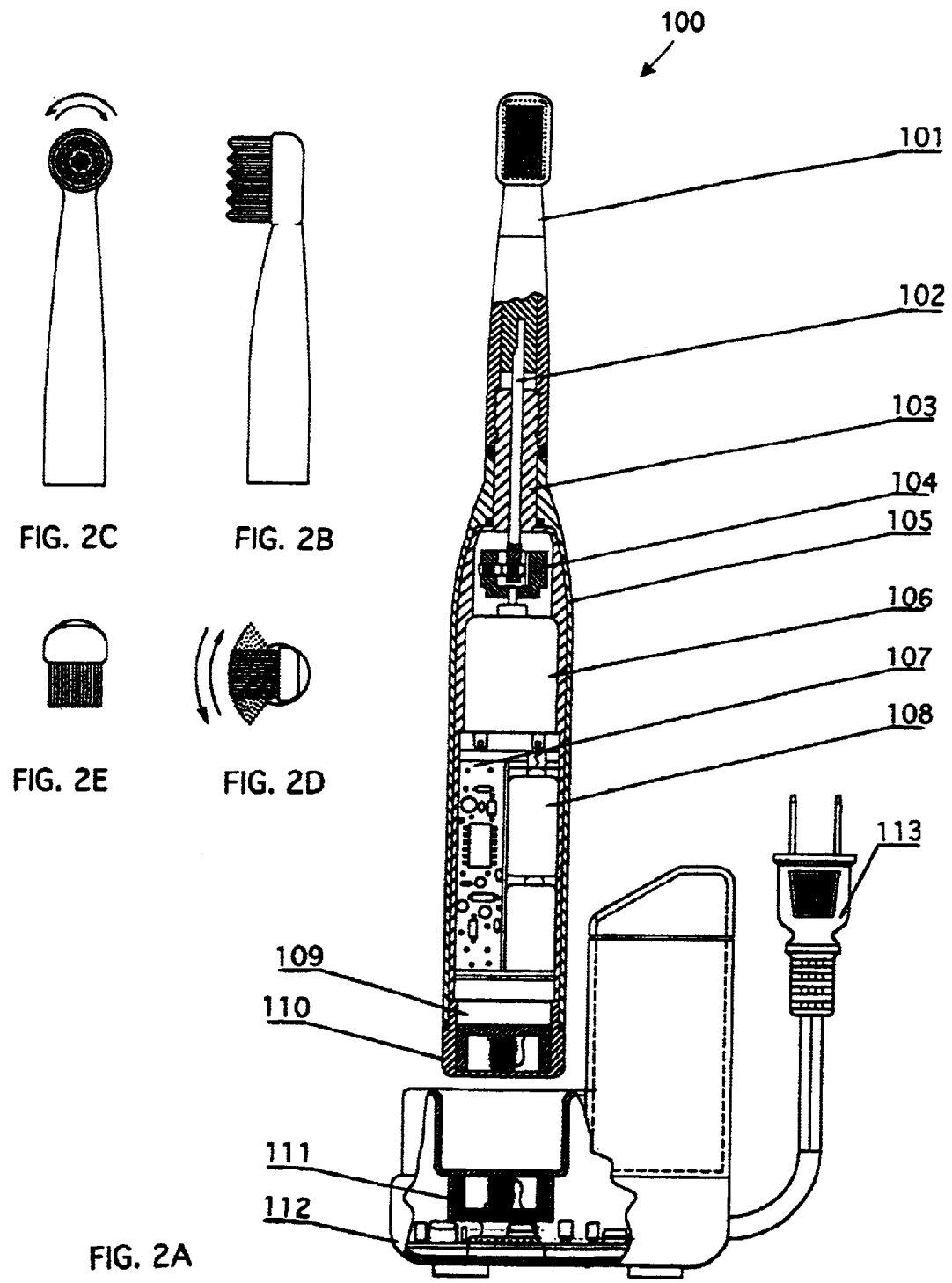
FIG. 2A is a cross sectional view of a toothbrush of this invention with a higher brush head vibration frequency that is multiple-times of the rotational frequency of a DC motor.
FIGS. 2B to 2C are front view and side-view respectively of a brush head of this invention.
FIGS. 2D to 2E are front view and side view of the vibrations of the bristles for the brush heads as shown in FIGS. 2B and 2C respectively.

Referring to FIG. 2A for a cross sectional view of a vibrating toothbrush 100 of this invention. The toothbrush includes an elongated hollow case 105 for enclosing and protecting the electrical and mechanical components contained in the case and also functions as a handle that a user of the toothbrush can conveniently hold and control and move the toothbrush. The elongated hollow case 105 is generally circular in cross section and includes a lower body portion and upper neck portion. The lower body portion has a length of about ten to fifteen centimeters and a diameter ranging from 2 to 4 centimeters. The upper neck portion has a length of about three to five centimeters and a diameter of about 0.5 to 1.0 centimeter. A brush head 101 is then mounted onto the upper neck. The side view and front view of the brush head 101 is shown in FIGS. 2B and 2C respectively. The brush head 101 with the bristles is powered by the rechargeable batteries 108 to vibrate as that shown in FIGS. 2D and 2E.

For the purpose of vibrating the toothbrush head 101, a vibrating arm 102 is provided to engage the head 101. The vibrating arm 102 is mounted onto a vibrating pivot 104. The vibrating pivot 104 is driven by a DC motor 106 to generate a vibrating movement. The structural details and the electromagnetic fields employed by the vibrating pivot to convert a rotational movement of the DC motor 106 to a vibration movement will be further described below. The DC motor 106 is driven by the power provided by rechargeable battery 108. Next to the rechargeable batteries 108 is the control circuit 107 that is provided for switching on/off and controlling the rotational speed of the DC motor 106 and consequently the vibration frequency of the lever arm 102 controls the operation of the toothbrush. A battery charging circuit, that includes an upper charging component 109 contained in the elongated hollow case protected by an outer shell 110, is disposed below the rechargeable batteries 108. The toothbrush is then designed for placement into a battery-charging base-placement device 112 that includes a lower charging component 111 that is provided to plug into an external AC power source via an AC power cord and plug 113 for charging the rechargeable batteries 108. The details of a novel and improved charging circuits implemented in the upper and lower charging components will be further described below.

Figure 3A:
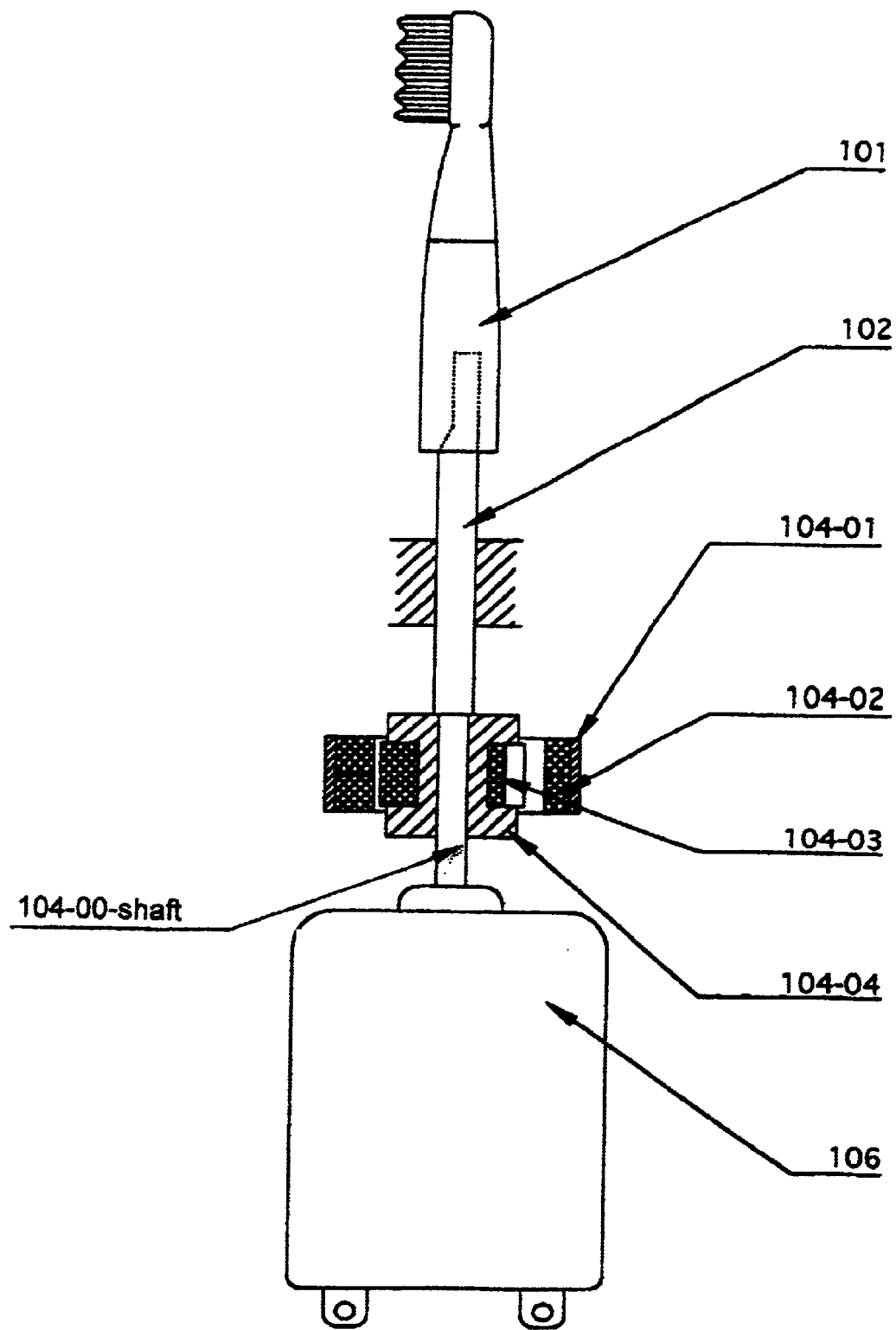
FIGS. 3A to 3F are functional diagrams for illustrating the direct mechanical-to-electromagnetic driving mechanism of this invention for generating high frequency vibrations.
Figure 3B:
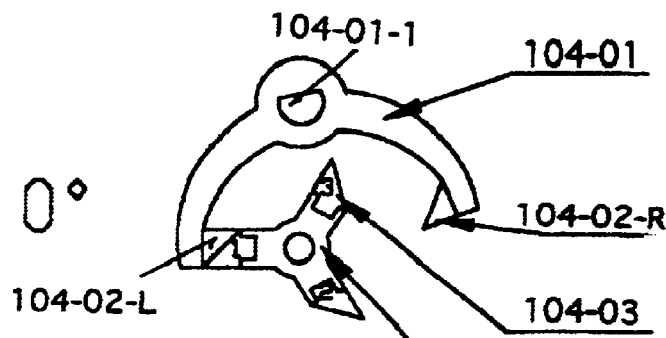
Figure 3C:
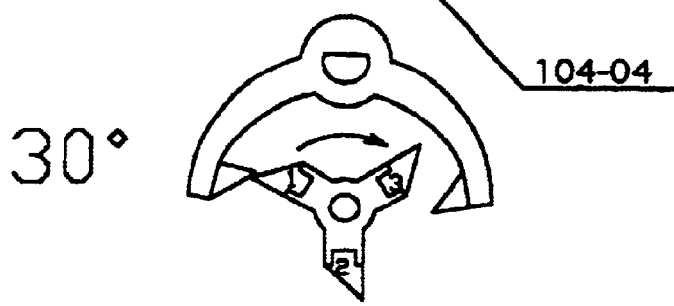
Figure 3D:
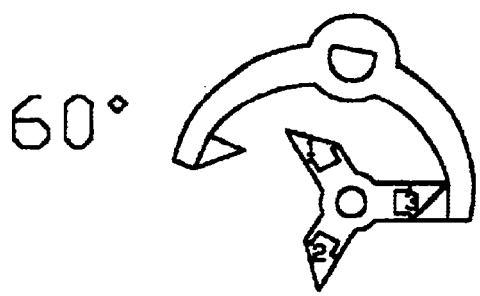
Figure 3E:
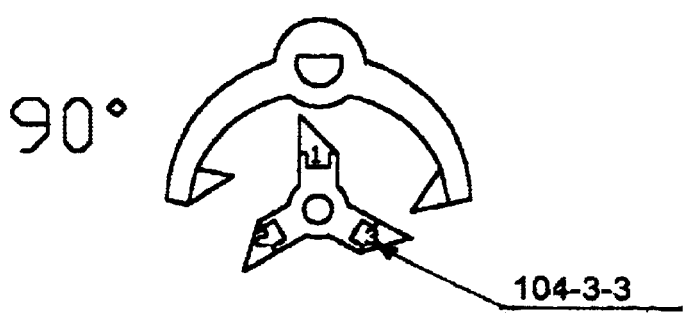
Figure 3F:
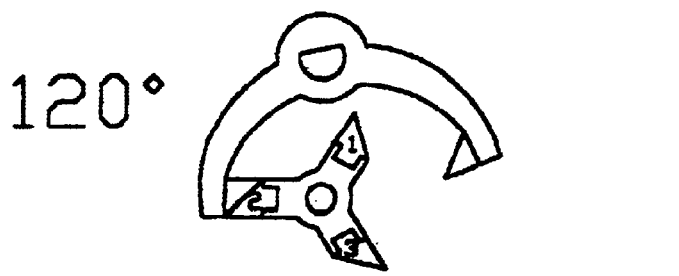

FIGS. 3A to 3F are functional diagrams to show the details of an embodiment of this invention for illustrating an example of a direct mechanical-electromagnetic driving mechanism. The direct mechanical-to-electromagnetic vibration mechanism is driven by a DC motor 106 mounted with a rotating shaft 104-04 attached to a three-leg permanent magnet 104-03 with each leg continuously rotating along a clockwise rotational direction. As shown in FIGS. 3B to 3F, the first leg 104-03-1 of the three-leg permanent magnet 104-03 first engages a left arm magnetic 104-02-L of a two-arm vibrating fork 104-01. The two-arm fork 104-01 vibrating along a shaft 104-00-shaft. With a strong repulsive force between the first leg 104-03-1 of the three-leg magnetic 104-03 and the left arm 104-2-L (FIG. 3B), the force pushes the vibrating fork 104-01 to rotate along the rotation shaft 104-01-shaft in a clockwise direction to a 30-degree position (FIG. 3C). And, because of the nearness of the left arm 104-02-L and the first leg 104-03-1, the vibrating fork 104-04 is continuously pushed to rotated in the clockwise direction to reach a 60-degree position (FIG. 3D). And, in the meantime, the three-leg permanent magnet 104-03 continuously rotates in the clockwise direction. The second leg 104-3-3 is moved to a position to engage the right arm magnet 104-02-R that is attached to the right arm of the two-arm vibrating fork 104-01 (FIG. 3D). The repulsive force between the second leg magnet 104-03-2 and the right arm magnet 104-02-R then push the two-arm vibrating fork 104-01 to rotate in a counterclockwise direction to reach a 90-degree position (FIG. 3E). Meanwhile, the three-leg permanent magnet 104-03 continuously rotates in the clockwise direction. The third leg 104-3-3 is moved to a position to engage the left arm magnet 104-02-R that is attached to the left arm of the two-arm vibrating fork 104-01 (FIG. 3F). The two-arm vibrating fork 104-01 is again pushed to rotate in a clockwise direction and start to repeat the 0–30–60–90–120 degrees clockwise-then-counterclockwise sequences of vibration movement as shown in FIGS. 3B to 3F. As shown in this direct rotational mechanical-to-magnetic vibration mechanism, the three-fold (3N) vibration frequency of the rotational frequency of the DC motor can be achieved where N is the rotational frequency of the DC motor. The vibrating level 102 that is attached to the vibrating pivot 104 is implemented as the rotation shaft 104-01-shaft can therefore vibrating clockwise and counterclockwise at a frequency of 3N. By providing a DC motor 106 to rotate at a frequency of 5000 to 7000 rotations per minute, a frequency of 30,000 to 40,000 toothbrush strokes per minute of the toothbrush head 101 can be easily achieved.

According to FIGS. 2 and 3, this invention discloses a vibrating toothbrush. The vibrating toothbrush includes an elongated hollow tube defining a toothbrush body 105 having a top-head end and a bottom-seat end. The toothbrush further includes a vibrating means 104 disposed near the bottom-seat end inside the hollow tube. The vibrating means 104 includes a two-arm fork 104-01 with a first fork and a second fork extended from a central portion. The first fork and second fork substantially extends semi-circularly opposite each other and having a first and second permanent magnets 104-02-L and 104-02-R attached to an end of the first and second fork respectively. The toothbrush further includes a vibrating lever arm 102 mounted on the central portion of the vibrating means 104 and extends therefrom toward the top-head end wherein the central portion rotating along a rotational axis defined by the vibrating lever arm 102. The toothbrush further includes a DC motor 106 for rotating a vibrating driving shaft 104-04 at a DC motor rotational frequency. The vibrating means 104 further comprises a multiple-arm permanent magnet 104-3 attached to and rotating with the vibrating driving shaft 104-4 driven by the DC motor 106. The multiple-arm permanent magnet 104-03 includes a plurality of extended arms extended from the vibrating driving shaft 104-04. The arms extend toward and rotationally approaching the first and second permanent magnets 104-02-L and 104-02-R for magnetically asserting a force on the two-arm fork for vibrating the two-arm fork and the vibrating lever arm attached thereto. In a preferred embodiment, the toothbrush further includes toothbrush head 101 mounted onto the toothbrush body 105 on the top-head end and mechanically coupled to and vibrating with the vibrating lever arm 102.

In summary, this invention discloses a vibrating toothbrush that includes an elongated hollow tube 106 defining a toothbrush body having a top-head end and a bottom-seat end. The toothbrush further includes a vibrating means 104 disposed near the bottom-seat end inside the hollow tube 106. The toothbrush further includes a vibrating lever arm 102 mounted on the vibrating means 104 and extends therefrom toward the top-head end. The toothbrush further includes a rotational means 106 for rotating a vibrating driving shaft 104-04 at a rotational DC motor and energy-transferably engaging the vibrating means 104 for generating a vibrating frequency higher than the rotational frequency.

Figure 4:
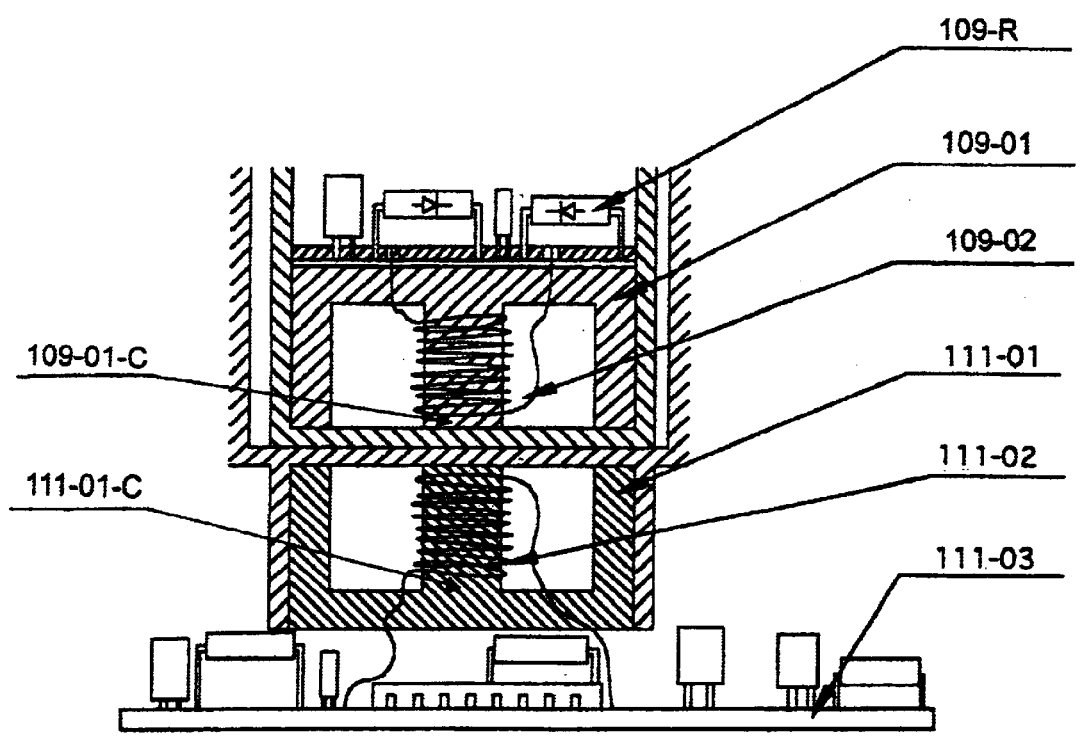
FIG. 4 is a partial cross sectional view of the charging components of the toothbrush for this invention for providing high charging capacity by applying a direct transformer-coupling charging configuration.

FIG. 4 is a functional diagram showing an improved battery-charging device for charging the rechargeable battery with higher charge current, e.g., a 1000 mA-hour charging capacity, to shorten the charging period requirement of the automatic toothbrush. The upper and lower charging components 109 and 111 each includes a ferrite E-core magnetic core 109-01 and 111-01 with coils 109-02 and 111-02 wrapping around the center ferrite magnetic core 109-01-C and 111-01-C respectively. The center magnetic core 109-01-C and 111-01-C are arranged to face each other when the tooth brush is made to sit onto the charging base 112. The lower charging component 111 further includes a frequency converter to convert the input AC current to a higher frequency. The lower and upper charging component 109 and 111 with the coil wrapped ferrite magnetic core 109-01-C and 111-01-C arranged as coupled transformer to induce a coupled inductive current in the upper charge component 109. The induced charging AC currents are then converted to DC charging currents by employing rectifiers 109-R. A high charging current of 160 mA can be easily achieved with this directly inductance-coupled transformer-type charging circuit. The charging rate is increased to 1000 mA-hour and the time to charge the rechargeable batteries to their full capacities is reduced from 16 to 24 hours to six hours.

According to FIGS. 2 and 4, this invention also discloses a charging system for an automatic toothbrush. The charging system includes a primary electromagnetic transformer means 111 disposed in a charging base for receiving an input AC current from an AC power source. The charging system further includes a secondary electromagnetic transformer means disposed in a bottom end of the toothbrush for immediately sitting on and electromagnetically coupling to the primary electromagnetic transformer means for generating an inductive secondary current as an AC input current for the charging system of the automatic toothbrush. In a preferred embodiment, the primary electromagnetic-transformer means 111 further includes a primary ferrite E-core 111-01. The secondary electromagnetic-transformer means 109 further includes a secondary ferrite E-core 109-01. The primary ferrite E-core 111-01 further include primary conductive coils 111-02 wrapping around a center ferrite-E core 111-01-C for inputting an AC primary current. The secondary ferrite E-core 109-01 further include secondary conductive coils 109-02 wrapping around a center ferrite-E core 109-01-C for inducing a secondary inductive AC current. In a preferred embodiment, the charging system further includes a frequency converter disposed in the charging base for converting an input AC current into an AC current of a higher frequency for improving an efficiency of electromagnetic transformation between the primary electromagnetic-transformer means and the secondary electromagnetic-transformer means. In a preferred embodiment, the charging system further includes a rectifier 109-R connected to the secondary conductive coil for converting the secondary AC current into a DC charging current for charging batteries of the automatic toothbrush. In a preferred embodiment, the rectifier 109-R generating a DC charging current greater than 160 mA. In a preferred embodiment the charging system is provided for charging the batteries at a rate greater than 1000 mA per hour.

Figures 5A, 5B:
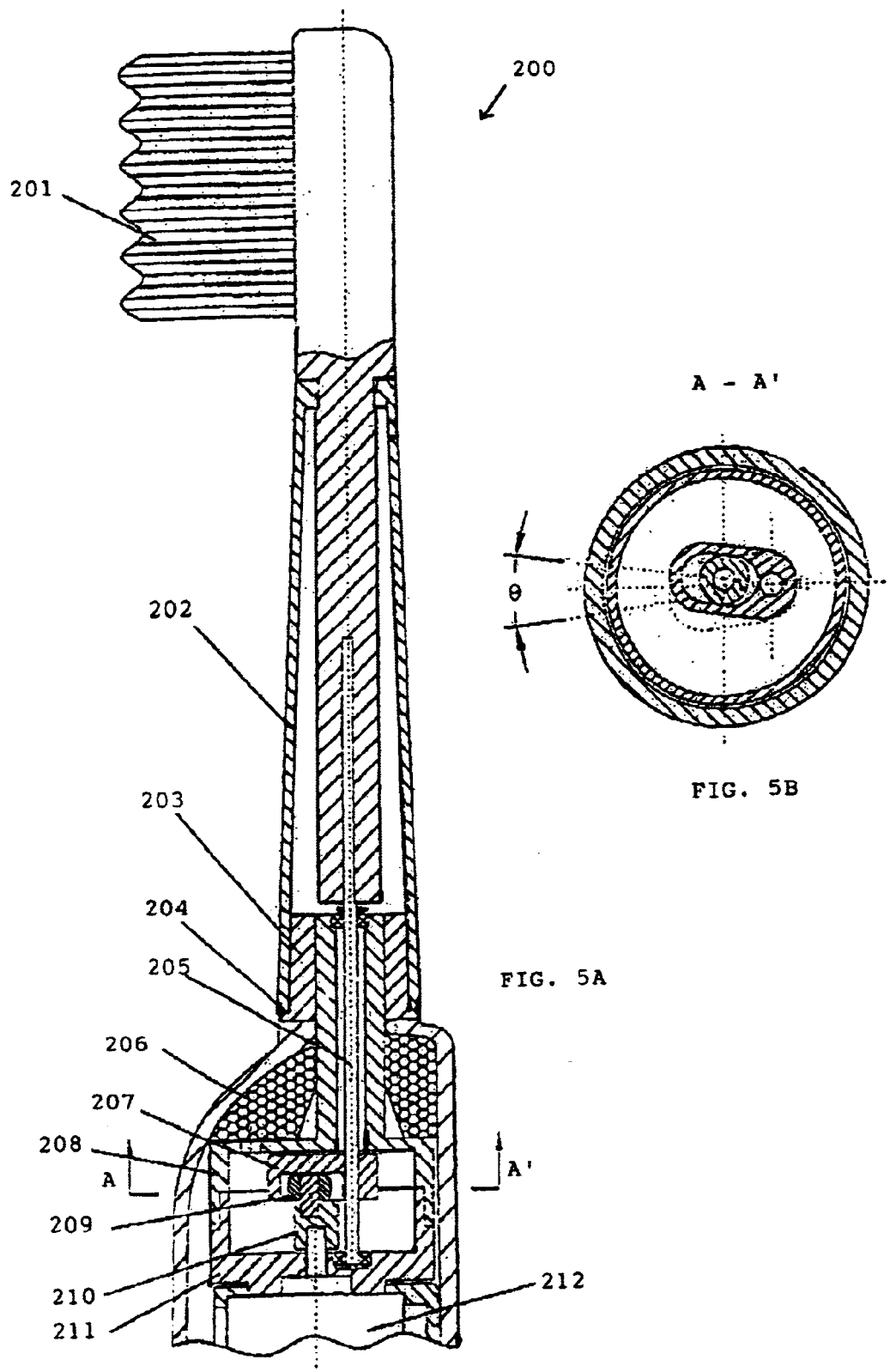
FIGS. 5A and 5B are a schematic diagram and top cross sectional view respectively for showing the structure and mechanical and electrical functions of different structural parts for a vibrating automatic toothbrush.

Referring to FIGS. 5A and 5B for another preferred embodiment of this invention. FIG. 5A is a schematic diagram for showing the mechanism that makes an automatic toothbrush 200 vibrates. The automatic toothbrush 200 has a toothbrush head 201 supported on is a cone shape cover 202. At the bottom of the cone shape cover 202 is a is a tubular adapter 203 that is extended from the bottom mouth of the toothbrush head unit supported on the cone shaped cover 202. A color circle 204 is placed around the cover 202 and the color circle 204 distinguishes the toothbrush head for use by different users. A swinging rod 205 is inserted into the central opening of the toothbrush head. A sponge cushion body 206 surrounds the portion supporting the swinging rod 205 to minimize vibration. A body cavity is opened in the toothbrush base unit that has two curve shaped troughs. As shown in FIG. 5B that is a top view along the line A-A', the opening is covered by a plastic cover 207 and a side cover 208. A shaft 209 the shaft is attached and driven by a turn table 210 covered by a bottom cover 211 and mechanical driven by a DC motor or DC motor 212.

When a battery or another electrical power source supplies power to the DC motor 212 to begin a rotation movement, the turntable 210 rotates concurrently with the DC motor. The shaft 209, which is attached to the turntable 210, will create a centrifugal movement. The centrifugal movement of the turntable 210 causes the plastic cover 207 attached to the shaft 209 to vibrate. Diagram A—A shows that the vibration angle θ, due to the swinging rod 205 is tightly fixed onto the plastic cover 207, this creates a simultaneous vibration. This vibration will be transferred to the toothbrush head. Therefore, the toothbrush head will also create a periodic vibration movement with an angular range θ in the vibration movements as shown in FIG. 5B.

Figure 6A:
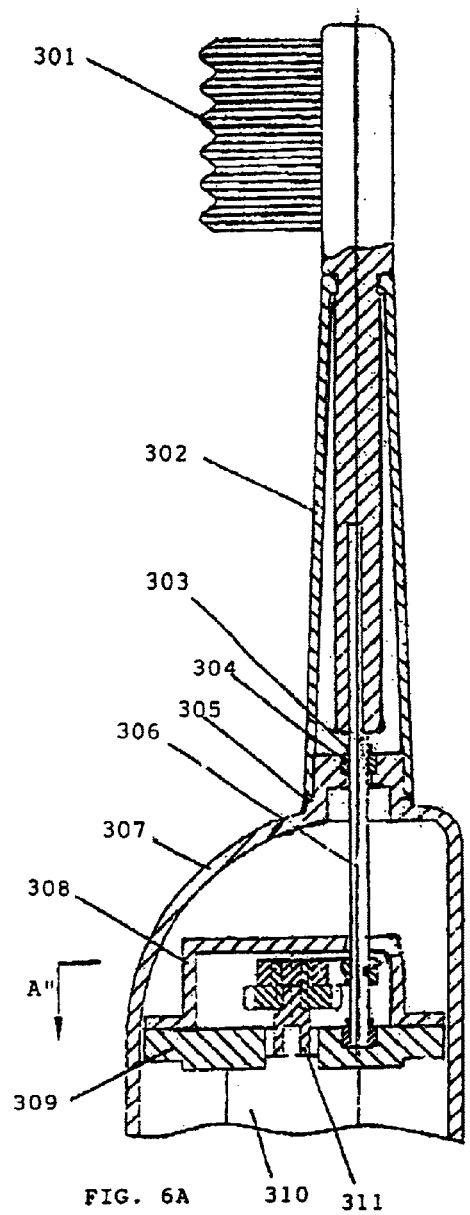
FIGS. 6A, 6B and 6C are a schematic diagram and top and side cross sectional views respectively for showing the structure and mechanical and electrical functions of different structural parts for an automatic toothbrush.
Figure 6B:
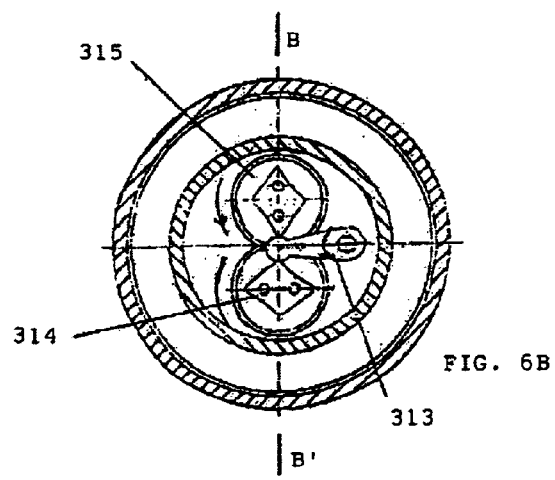
Figure 6C:
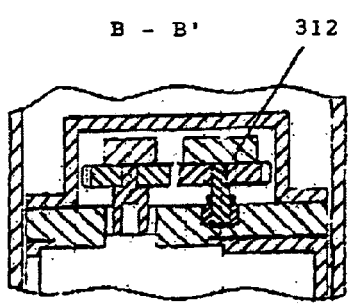

FIGS. 6A to 6C show another embodiment of this invention implemented with a different vibration mechanism for driving an electric toothbrush 300. Similar to FIG. 5A, a toothbrush bead 301 is supported on a cone shape cover 302. At the bottom of the cone shape cover 302 is a locking screw 303 for locking the toothbrush head to the base unit. A shaft 304 extends in the central portion of the toothbrush head to engage the toothbrush head to the base unit. A color circle 305 is placed around the cover 302 and the color circle 304 distinguishes the toothbrush head for use by different users. A swing rod 306 extends from the base unit to engage the shaft 304 for vibrating the toothbrush head. The base unit 307 has a body cavity and covered with a top cover 308 and supported with a support platform 309. At the bottom of the body cavity is an electric DC motor 310 engaged to a cone shaped cover 311 covering over lead gear to be further illustrated in FIGS. 6B and 6C. FIG. 6B shown a top view along a cutoff line A"-A'". A diamond shape convex step 314 is a implemented in each of the two identical gears 315. The two steps are parallel to each other for driving a pendulum 313 with a circular head. As shown in a side cross sectional view cutoff along line B–B' in FIG. 6C, a rotor 312 is provided for another set of gears.

When the DC motor 310 engaging to the cone shape cover 311 for moving one of the parallel gears 315, the other gear is also driven and moved accordingly. The two gears 315 rotate in opposite directions. The diamond shape steps 314 on the gears 315 will also rotate in opposite directions. The pendulum 313 in between the two steps 314 will be hit and swings back and forth. The circular head circles the center of one end and rotates to a certain angle, the step after rotating 90 degrees will cease to contact with the pendulum 313. The opposite step will push the circular head to move to an opposite direction, and return to its initial position. When the step turns 90 degrees, it will cease to contact with the pendulum 313. Thus creating a periodic movement. Since the swinging rod 306 is tightly fixed through the pendulum 313, and is also the center of the vibration, when the pendulum swings, the swinging rod will swing. This in turn causes the toothbrush head to vibrate. When the gear 315 rotates 180 degrees, the pendulum will complete a cycle. When the gear rotates 360 degrees, the pendulum swings twice. Therefore, the swinging frequency of swinging rod 306 is twice the frequency of the DC motor 310. This is another advantage of the invention.

Figures 7A, 7B:
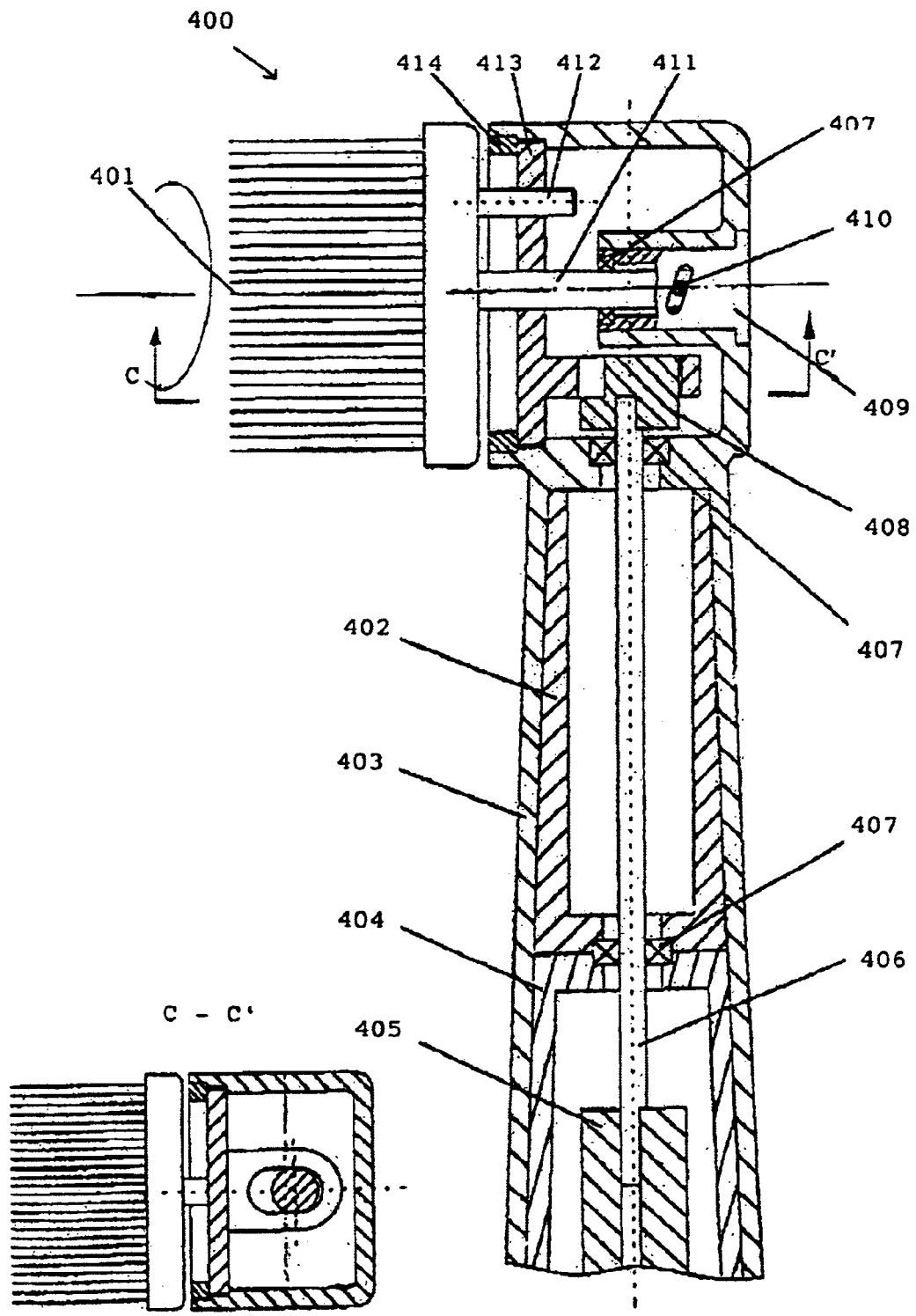
FIGS. 7A, and 7B are a schematic diagram and side cross sectional views respectively for showing the structure and mechanical and electrical functions of different structural parts for an automatic toothbrush.

Referring to FIGS. 7A to 7B for a novel toothbrush structure for showing a mechanism to create three-dimensional (3-D) movement on the toothbrush head 400. The 3-D movement head 400 has a rotational brush 401 supported on a head body that has an inner body cover 402 and outer cover 403. The head body has a lower portion that has a bottom inner cover 404 and a connecting cover 405. A vibrating rod 406 extends in central housing along the vertical direction of the head 400 engaging a shaft 407 and an off center shaft 408. A center-cover 409 with an inclined trough for includes a locking screw 410 is a locking screw for driving a central shaft 411 that is fixed onto the toothbrush plate. A connecting screw plate 413 surrounded by a fixing ring 414.

The operation of the 3-D toothbrush head is achieved by a transfer of the vibration of the toothbrush shaft 406 through the connecting cover 405. The shaft 406 consequently causes the off center shaft 408 to vibrate or swing. Referring to FIG. 7B for a side cross sectional view cutoff along line C-C'. The off center shaft 408 is located under the trough of 413. When the off center shaft 408 rotates, it will lead the plate 413 to swing along shaft 411. Through the connecting screws 412, the toothbrush plate 401 will vibrate perpendicular to the central shaft 411. Since the central shaft 411 is fixed on the toothbrush plate, it will follow and vibrate. The locking screw 410 is in the inclined trough. When it swings, it causes the shaft 411 and the toothbrush plate to swing back and forth along the shaft. A combination of these mechanisms, the toothbrush is enabled to vibrate in a periodic three-dimensional movement. From the above analysis, it is clearly disclosed that new methods and configurations are provided in addition to a direct left-right swing motion driving mechanism to drive an automatic toothbrush as that typically available in the commercial products. In this invention, simple rotational movement generator by a electrical DC motor or generator of this invention can be converted to a swing motion, rotation motion and motions at different directions to produce a multiple dimensional, e.g., 3-D, motions.

Figure 8:
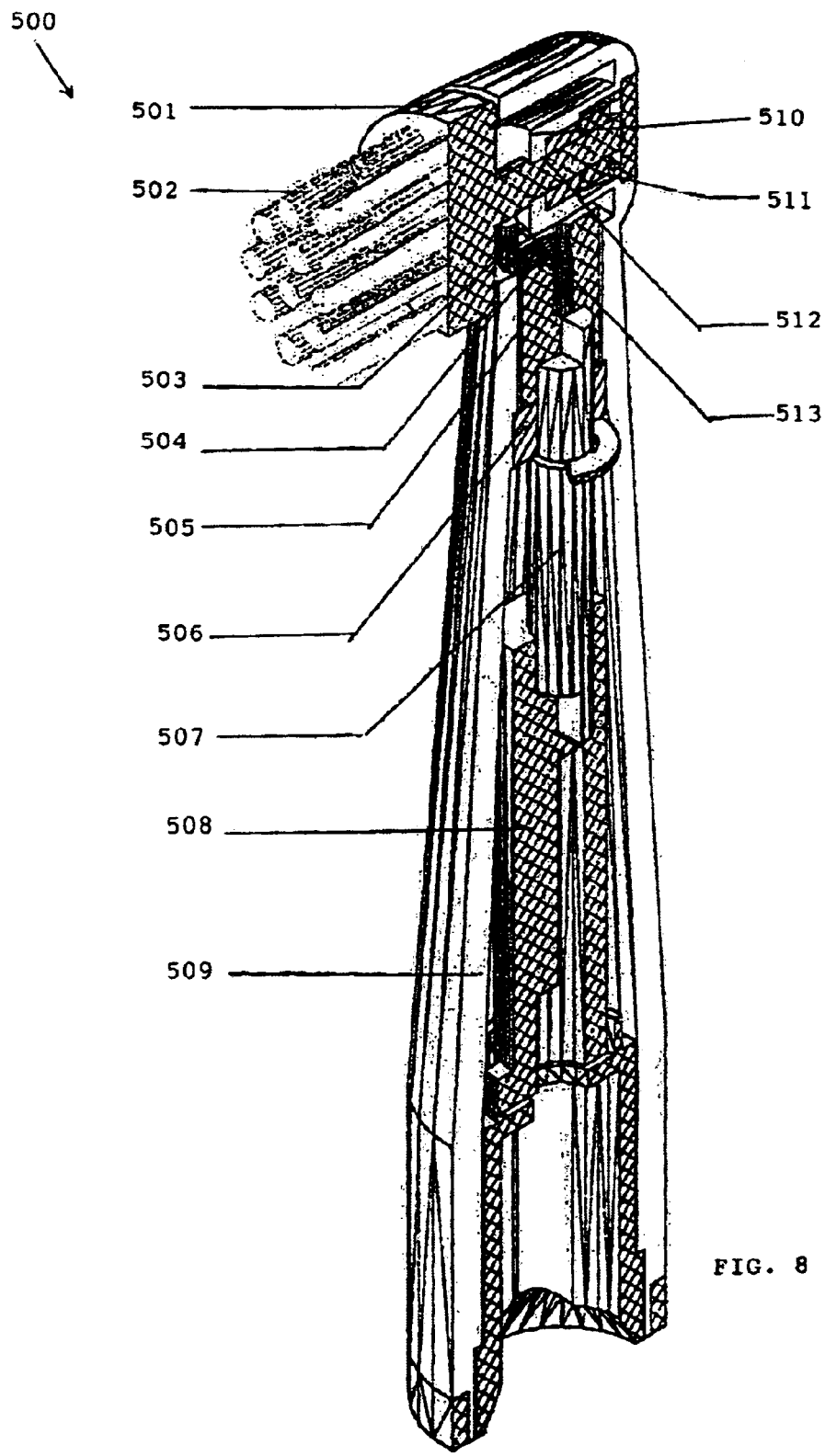
FIG. 8 is a perspective view of a toothbrush head for an automatic toothbrush of this invention.

Referring to FIG. 8 of another preferred embodiment of a toothbrush head 500 of this invention. The toothbrush bristles 502 are formed and supported on a plate 501 with a shaft 512 fixed onto the plate 501. The shaft 512 is engaged to a shaft holder 510 through a spacer 511. A head Z-shaped wire 504 is fixed onto the plate 501 with two fixed-nails 513 on a head attachment point 503. The Z-wire 505 is engaged to a rotor 505 for moving with the rotor for the purpose of generating a corresponding movement of the head plate 501 and the bristles 502. The toothbrush head further includes brush 506 to electrically operate with the rotor to generate the rotor movement. A linking shaft 507 extends from the rotor into a cavity of a connecting pipe 508 to engage to the toothbrush vibration generating mechanism supported in a toothbrush base unit as discussed above. The toothbrush head 500 further has a body 509 that has a bottom adapting opening to plug onto a toothbrush unit with the linking shaft 507 engaged to a head-movement mechanism for generating the vibration and bristle movements.

Therefore, this invention provides an automatic power toothbrush capable of vibrating or rotating at higher frequency and can be charged with higher charging capacities such that the difficulties and limitations encountered in the prior art can be overcome. Specifically, an improved automatic power toothbrush driven by a direct mechanical to electromagnetic driving mechanism is disclosed. More direct and efficient utilization of electric power by direct coupling of the mechanical rotation and the electromagnetic force is provided with power supplied by the rechargeable batteries. Higher vibrating frequencies are made available by employing this improved driving mechanism. This invention also discloses an improved automatic power toothbrush charged by a direct AC-to-AC current transformer charging circuit to provide higher charging capacity. The charging efficiency is further improved and optimized with a frequency converter to convert a regular AC current to a primary current of higher frequency to generate a secondary induced current applicable for efficiently charging the rechargeable batteries. Shorter charging period is achieved with higher charging capacity. More economic use of the toothbrush is now achievable with multiple users using multiple brush heads when the charging period is shortened. More direct and convenient control of the vibrating speed is now achievable by simply varying the rotational speed of the DC motor. The user is provided with more convenient options to vary the brushing speed by a speed variation control switch with more precise control mechanism because the direct mechanical to electromagnetic coupling in driving the power toothbrush.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. A vibrating toothbrush comprising:
   an elongated hollow tube defining a toothbrush body having a top-head end and a bottom-seat end;
   a vibrating means disposed near said bottom-seat end inside said hollow tube wherein said vibrating means comprising a two-arm fork with a first fork and a second fork extended from a central portion wherein said first fork and second fork substantially extends semi-circularly opposite each other and having a first and second permanent magnets attached to an end of said first and second fork respectively;
   a vibrating lever arm mounted on said central portion of said vibrating means and extends therefrom toward said top-head end wherein said central portion rotating along a rotational axis defined by said vibrating lever arm; and
   a DC motor for rotating a vibrating driving shaft at a DC motor rotational frequency;
   said vibrating means further comprising a multiple-arm permanent magnet attached to and rotating with said vibrating driving shaft driven by said DC motor wherein said multiple-arm permanent magnet having a plurality of extended arms extended from said vibrating driving shaft toward and rotationally approaching said first and second permanent magnets for magnetically asserting a force on said two-arm fork for vibrating said two-arm fork and said vibrating lever arm attached thereto.

2. The vibrating toothbrush of claim 1 further comprising:
   a toothbrush head mounted onto said toothbrush body on said top-head end and mechanically coupled to and vibrating with said vibrating lever arm.

3. A vibrating toothbrush comprising:
   an elongated hollow tube defining a toothbrush body having a top-head end and a bottom-seat end;
   a vibrating means disposed near said bottom-seat end inside said hollow tube;
   a vibrating lever arm mounted on said vibrating means and extends therefrom toward said top-head end;
   a rotational means for rotating a vibrating driving shaft at a rotational frequency and energy-transferably engaging said vibrating means for generating a vibrating frequency higher than said rotational frequency;
   said vibrating means further comprising a two-arm fork with a first fork and a second fork extended from a central portion wherein said first fork and second fork substantially extends semi-circularly opposite each other and having a first and second permanent magnets attached to an end of said first and second fork respectively;
   said central portion engaging said vibrating lever arm and rotating along a rotational axis defined by said vibrating lever arm; and
   said vibrating means further comprising a multiple-arm permanent magnet attached to and rotating with said vibrating driving shaft driven by said rotation means wherein said multiple-arm permanent magnet having a plurality of extended arms extended from said vibrating driving shaft toward and rotationally approaching said first and second permanent magnets for magnetically asserting a force on said two-arm fork for vibrating said two-arm fork and said vibrating lever arm attached thereto.

4. The vibrating toothbrush of claim 3 wherein:
   said multiple-arm magnet comprising three extended arms extended from said vibrating driving shaft at positions represented by phase angles of substantially one-hundred-and-twenty degrees apart from each other for vibrating said two-arm fork at substantially at a vibrating frequency three-times of a rotational frequency of said vibration driving shaft.

* * * * *